United States Patent [19]

Bianchi et al.

[11] Patent Number: 4,985,366
[45] Date of Patent: Jan. 15, 1991

[54] PROCESS FOR THE ENZYMATIC RESOLUTION OF THE OPTICAL ISOMERS OF RACEMIC ESTER DERIVATIVES OF 3-MERCAPTO-2-ALKYL-PROPIONIC ACID

[75] Inventors: Daniele Bianchi, Milan; Pietro Cesti, Trecate; Paolo Golini, Turbigo, all of Italy

[73] Assignee: Montedison S.p.A, Italy

[21] Appl. No.: 357,949

[22] Filed: May 30, 1989

[30] Foreign Application Priority Data

Jun. 2, 1988 [IT] Italy ................................. 20834 A/88

[51] Int. Cl.$^5$ .............................................. C12P 7/62
[52] U.S. Cl. ...................................... 435/280; 435/135
[58] Field of Search ................................. 435/280, 135

[56] References Cited

PUBLICATIONS

Kagawa et al.—Chem. Abst., vol. 105 (1986), p. 5202p.
Sakimae et al.—Chem. Abst., vol. 105 (1986), p. 15176e.
Sakimae et al.—Chem. Abst., vol. 103 (1985), p. 36173t.

Primary Examiner—Sam Rosen
Attorney, Agent, or Firm—Morgan & Finnegan

[57] ABSTRACT

The biotechnological resolution by means of stereoselective enzymatic thio-transesterification of the racemic mixture of the optical isomers of the compounds of formula (I):

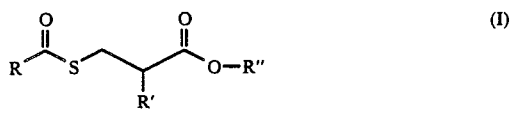

wherein:

R, R' and R", alike or different form one another, represent a linear alkyl group of from $C_1$ to $C_4$, in the presence of an alcohol and an enzyme capable of selectively causing the reaction of thio-transesterification of the (L)-isomer to take place, with the (D)-isomer remaining substantially unchanged, and being then separated by means of per se known techniques.

14 Claims, No Drawings

PROCESS FOR THE ENZYMATIC RESOLUTION OF THE OPTICAL ISOMERS OF RACEMIC ESTER DERIVATIVES OF 3-MERCAPTO-2-ALKYL-PROPIONIC ACID

DESCRIPTION OF THE PRESENT INVENTION

The present invention relates to a process relating to the enzymatic separation of the (D)- and (L)-optical isomers of racemic ester derivatives of 3-mercapto-3-methyl-propionic acid.

More particularly, the present invention relates to a biotechnological process for the separation, or resolution, of the optical isomers of the compounds of formula (I):

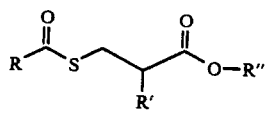

wherein:
R, R' and R", independently from one another, represent a linear alkyl group of from $C_1$ to $C_4$, carried out in the presence of enzymes endowed with esterasic activity, derived from microorganisms.

The compounds of formula (I), in particular as the optical (D)-isomers, are an important class of intermediates which are advantageously used in the synthesis of drugs with antihypertensive action (e.g., Captopril).

On the other hand, those skilled in the art know [D. W. Cushman, M. S. Cheung, E. F. Sabo and M. A. Ondetti, Biochemistry, 16, 5484 (1977)] that the potentiality of such drugs as inhibitors of angiotensin-converting drugs is strictly related to the configuration of the mercaptoalkanoic chain. In particular, the (D)-isomer is 100 times more active than the corresponding (L)-isomer.

Therefore the interest, by those dealing with organic syntheses, of having available an efficacious method for the separation of the optically active isomers, i.e., of the (D)-isomer from the (L)-isomer of the racemate of formula (I), becomes evident.

Examples of methods for carrying out the resolution of derivatives of 3-mercapto-2-methyl-propionic acid, and in particular of 3-acyl-mercapto-2-methyl- or -alkyl-propionic acids are known. Such methods respectively use the formation of diastereoisomer salts with optically active amines (EP-A-0 008 833) or the stereoselective enzymatic hydrolysis of corresponding esters (EP-A-0 130 752 and EP-A-0 172 614).

Such methods show drawbacks from the viewpoint of their application on an industrial level, in that they use expensive resolving agents, or they do not make it possible to obtain products with a high optical purity.

Therefore, the need was felt for having available a method suitable for being operated at an industrial level, and which makes possible the separation from each other of the optical isomers of ester derivatives of 3-mercapto-2-alkylpropionic acids, as above defined, in a simple, efficacious and cheap way.

The present invention therefore provides a process for the separation or resolution of the optical isomers of the derivatives of 3-mercapto-2-alkyl-propionic acids of formula (I) in a simple, efficacious, cheap way, and with a high degree of optical purity of these optical isomers In accordance with the present invention, it has now been discovered that this may be achieved by a selective enzymatic thio-transesterification of the racemates of the compounds of formula (I), using a particular class of enzymes, as more fully described in the following:

In practice, an enzyme is used which belongs to the class of microorganism-derived lipases, capable of causing thio-transesterification to take place stereoselectively on the (L)-form of the racemates of the compounds of formula (I), while leaving the (D)-isomer substantially unchanged.

Therefore, the object of the present invention is a process for the enzymatic separation of the racemic mixture of the optical isomers of the compounds of formula (I):

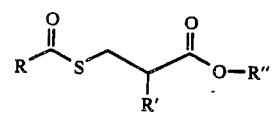

wherein:
R, R' and R", independently of one another, represent a linear alkyl group of from $C_1$ to $C_4$, which process is characterized in that a racemic compound substrate of formula (I) is reacted with an alcohol of formula (II):

$$R'''-OH \qquad (II)$$

wherein:
R''' represents a linear $(C_1-C_8)$-alkyl group, in the presence of a lipase derived from microorganisms, either free or immobilized on a porous support, which is capable of selectively causing the reaction of thio-transesterification of the (L)-isomer to take place, while leaving substantially unchanged the (D)-isomer of the compound of formula (I) used as the starting compound, which (D)-isomer is then separated by per se known techniques.

The racemic compounds of formula (I) used as the starting compounds are per se known and may be synthesized according to conventional techniques (EP-A-0-172 614).

According to a schematic representation of the process according to the present invention, the racemic esters of formula (I) are reacted in the presence of an enzyme of the type above defined, with an alkyl alcohol of formula (II) according to the reaction scheme:

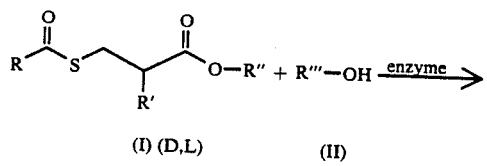

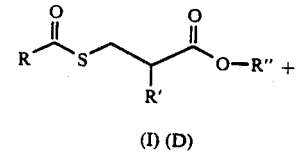

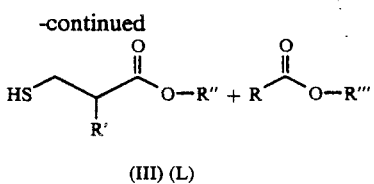

(III) (L)

wherein R, R" and R'" have the above meanings.

Preferred alkanols of formula (II) are ethanol, propanol, butanol, and so forth.

These alcohols are used in an amount in excess referred to the substrate of formula (I), in that they are used in the reaction both as reactants and as solvents. In particular, molar ratios of said alcohols of formula (II) to said ester of formula (I) are used which are within the range of from 3:1 to about 100:1, and preferably within the range of from 5:1 to about 10:1.

The weight ratio of the enzyme to the substrate of formula (I) is within the range of from 1:5 to 1:50, and preferably within the range of from 1:10 to about 1:20.

The process of thio-transesterification is carried out by vigorously stirring the reaction mixture constituted by the reactant (I), dissolved in the alcohol (II) simultaneously acting as a reactant and a solvent, and by the enzyme, which is either free or supported, as disclosed below in greater detail, at temperatures within the range of from 10° to 60° C., and preferably within the range of 20° C. to about 30° C.

At the end of the reaction, the enzyme is filtered off, whereupon it may be recovered and used again.

From the filtrate, which consists of the organic reaction phase, the ester (I) in the (D)-form and the thiol (II), in the (L)-form, are separated by using such traditional means as column chromatography.

As an alternative, the thiol of formula (II) may be extracted from the reaction mixture, after dilution with a solvent immiscible with water (for example, ethyl ether, dichloromethane, and so forth), by means of a simple washing with an aqueous solution of NaOH at 5%.

The optical purity of the esters of formula (I), obtained as described above, was determined above all by using N.M.R. techniques in the presence of europium complexes.

The absolute configuration of such esters was determined by comparing the 3-mercapto-2-alkyl-propionic acid obtained after acidic hydrolysis to the data available from the technical literature (M. Shimazaki et al., Chem. Pharm. Bull 30 (9), 3139, 1982).

The enzymes used in the present invention belong to the class of the lipases of microbial origin.

In particular, P. Lipase and CES Lipase, both derived from Pseudomonas, traded by Amano Pharm. Co., Japan, and respectively derived from *Pseudomonas fluorescens* and from Pseudomonas sp., have been shown to be active.

According to the present invention the enzymes may be used either free or immobilized on suitable supports in order to increase their activity and stability, and to make easier their recovery. Porous supports having a high surface areas such as, e.g., celite, porous glass, Amberlite XAD 7, Amberlite XAD 8, and so forth (trade names by Rohm and Haas-U.S.A.), have been shown to be particularly suitable for the intended purpose.

The immobilization may be carried out easily by causing a buffered aqueous solution of the enzyme to be adsorbed on the support, and then evaporating the solvent to dryness.

EXAMPLES

The present invention is now illustrated by the following examples, which however are given merely for illustrative and non-limitative purposes.

The abbreviation "e.e." used hereinafter means "enantiomeric excess."

EXAMPLE 1

Immobilization of Amano P Lipase on Celite

To 1 g of celite 577 (traded by Johns Manville, Ltd., Richmond Surrey), is added 250 mg of Amano P Lipase enzyme dissolved in 5 ml of 0.1 N Na/K phosphate buffer, pH 7.

The so-obtained mixture is mixed, so as to obtain a homogeneous distribution of the enzyme, which is then dried in air at 20° C. for 18 hours.

Separation of the enantiomers of methyl 3-acetyl-thio-2-methyl-propionate

To a solution of 2 g of methyl 3-acetyl-thio-2-methyl-propionate in 6 ml of n-propanol, 120 ml of Amano P Lipase immobilized on 480 mg of celite is added.

The mixture is vigorously stirred at the temperature of 20° C., and the reaction is monitored by gas-chromatography.

After 48 hours (57% conversion), the supported enzyme is recovered by filtration and propanol is recovered under reduced pressure.

The residue is chromatographed on a silica gel column, using a 9/1 vol/vol mixture of hexane/ethyl ether as the 790 mg of methyl 3-acetyl-2-D-methyl-propionate as a colorless oil with $[\alpha]_D^{20} = -60.1$ (C=1, CHCl$_3$), e.e. =88%, and 850 mg of methyl 3-mercapto-2-L-methyl-propionate as a colorless oil with $[\alpha]_D^{20} = +16$ (C=1, CHCl$_3$) are obtained.

EXAMPLE 2

Separation of the enantiomers of methyl 3-acetyl-thio-2-methyl-propionate

The process is carried out under the same conditions as in Example 1, but using 120 mg of Amano CES Lipase instead of Amano P Lipase.

After 30 hours (conversion of 56%), the supported enzyme is recovered by filtration and the products are separated as described above.

750 mg of methyl 3-acetylthio-2-D-methyl-propionate with $[\alpha]_D^{20} = -61.1$ (C=1, CHCl$_3$), e.e. =90%, and 860 mg of methyl 3-mercapto-2-L-methyl-propionate with $[\alpha]_D^{20} = +15.9$ (C=1, CHCl$_3$) are obtained.

EXAMPLE 3

Separation of the enantiomers of propyl 3-acetyl-thio-2-methyl-propionate

The process is carried out under the same conditions as in Example 1, but using 2 g of propyl 3-acetyl-thio-2-methyl-propionate.

After 48 hours (conversion of 55%), the immobilized enzyme is recovered by filtration.

The alcoholic solution is diluted with 50 ml of ethyl ether and is washed with 50 ml of a solution of NaOH at 5%.

The organic phase is thoroughly dried over sodium sulphate and the solvent is evaporated under reduced pressure.

The residue is constituted by 88 mg of propyl 3-acetylthio-2-D-methyl-propionate, a colorless liquid with $[\alpha]_D^{20} = -48.9$ (C=1, CHCl$_3$), e.e.=92%.

EXAMPLE 4

Separation of the enantiomers of propyl 3-acetyl-thio-2-methyl-propionate

The process is carried out under the same conditions as in Example 3, but using 7 ml of n-butanol instead of n-propanol.

After 24 hours (conversion of 57%), the supported enzyme is recovered by filtration and the residue is treated as described above. 790 mg of propyl 3-acetylthio-2-D-methyl-propionate is obtained as a colorless liquid with $[\alpha]_D^{20} = -51.8$ (C=1, CHCl$_3$), e.e.=95%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

What is claimed is:

1. Process for the enzymatic separation of the racemic mixture of the optical isomers of the compounds of formula (I):

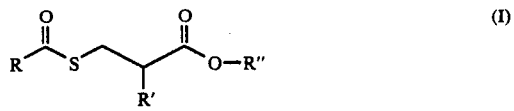

wherein:

R, R' and R", independently of one another, represent a linear alkyl group of from C$_1$ to C$_4$, which process comprises a racemic compound substrate of formula (I) being reacted with an alcohol of formula (II):

R'''—OH  (II)

wherein:

R''' represents a linear (C$_1$-C$_8$)-alkyl group in the presence of a lipase derived from microorganisms, which is capable of selectively causing the thio-transesterification of the (L)-isomer to take place, while leaving substantially unchanged the (D)-isomer of the compound of formula (I) used as the starting compound, which is then separated.

2. Process according to claim 1, wherein the alcohol of formula (II) is selected from the group consisting of ethyl alcohol, propyl alcohol and butyl alcohol.

3. Process according to claim 1 or 2, wherein said alcohol of formula (II) is used in an amount in excess referred to the racemic compound substrate of formula (I).

4. Process according to claim 3, wherein the molar ratio of said alcohol of formula (II) to said substrate of formula (I) is within the range of from 3:1 to about 100:1.

5. Process according to claim 4, wherein said molar ratio of said alcohol of formula (II) to said substrate of formula (I) is within the range of from 5:1 to about 10:1.

6. Process according to claim 1 or 2, wherein the process is carried out according to a weight ratio of the enzyme to said substrate of formula (I) which is within the range of from 1:5 to about 1:50.

7. Process according to claim 6, wherein said weight ratio of the enzyme to the substrate of formula (I) is within the range of from 1:10 to about 1:20.

8. Process according to claim 1 or 2, wherein said process is carried out at a temperature within the range of from 10° C. to about 60° C.

9. Process according to claim 8, wherein said process is carried out at a temperature within the range of from 20° C. to about 30° C.

10. Process according to claim 1 or 2, wherein said lipase of microbial origin is a lipase derived from Pseudomonas.

11. Process according to claim 10, wherein said lipase is selected from the class consisting of P Lipase derived from *Pseudomonas fluorescens* and CES Lipase derived from Pseudomonas sp.

12. Process according to claims 1 or 2, wherein said enzyme is used in a free state.

13. Process according to claim 1 or 2, wherein said enzyme is used in an immobilized state on a support selected from the group consisting of celite, porous glass, and amberlite.

14. Process according to claim 13, wherein the support is porous and has a high surface area.

* * * * *